United States Patent [19]

Kessler

[11] Patent Number: 5,227,161
[45] Date of Patent: Jul. 13, 1993

[54] METHOD TO CLEAN AND DISINFECT PATHOGENS ON THE EPIDERMIS BY APPLYING A COMPOSITION CONTAINING PEROXIDASE, IODIDE COMPOUND AND SURFACTANT

[75] Inventor: Jack H. Kessler, Ashland, Mass.

[73] Assignee: Symbollon Corporation, Sudbury, Mass.

[21] Appl. No.: 681,447

[22] Filed: Apr. 4, 1991

Related U.S. Application Data

[63] Continuation of Ser. No. 515,332, Apr. 27, 1990, abandoned, which is a continuation of Ser. No. 240,212, Sep. 6, 1988, abandoned.

[51] Int. Cl.$^5$ .......................... C11D 3/48; A61K 37/50
[52] U.S. Cl. .................... 424/94.4; 252/100; 252/173; 252/174.12; 252/DIG. 5; 252/106; 422/37; 424/613; 424/667; 424/668; 424/669; 424/670; 424/671
[58] Field of Search ................. 252/100, 106, DIG. 5, 252/173, 174.12; 422/37; 424/94.4, 613, 667, 668, 669, 670, 671

[56] References Cited

U.S. PATENT DOCUMENTS

| | | | |
|---|---|---|---|
| 3,282,777 | 11/1966 | Ceriotti | 424/671 |
| 3,728,449 | 4/1973 | Cantor et al. | 424/671 |
| 3,966,090 | 6/1976 | Prussin et al. | 222/94 |
| 4,012,504 | 3/1977 | Eckols | 424/667 |
| 4,067,967 | 1/1978 | Prince | 424/667 |
| 4,140,766 | 2/1979 | Kalogris | 424/667 |
| 4,414,127 | 11/1983 | Fu | 252/95 |
| 4,485,029 | 11/1984 | Kato et al. | 252/106 |
| 4,576,817 | 3/1986 | Montgomery et al. | 424/94 |
| 4,588,586 | 5/1986 | Kessler et al. | 424/94 |
| 4,670,178 | 6/1987 | Huth | 252/95 |
| 4,808,328 | 2/1989 | Flohr | 424/667 |
| 4,814,109 | 3/1989 | Wittpen, Jr. et al. | 252/547 |
| 4,935,248 | 6/1990 | Witken | 424/671 |
| 4,937,072 | 6/1990 | Kessler et al. | 424/94.4 |
| 4,996,146 | 2/1991 | Kessler | 435/28 |
| 5,055,287 | 10/1991 | Kessler | 424/669 |
| 5,169,455 | 12/1992 | Kessler | 424/613 |

Primary Examiner—Paul Lieberman
Assistant Examiner—Bradley A. Swope

[57] ABSTRACT

This invention relates to a disinfecting epidermal cleaner using peroxidase, peroxide and iodide. The active components are maintained inactive until admixed in a define proportion with water. The pH at which the peroxidase is stored is between 7.0 and 9.0 and the pH of the admixture of the active components is between 3.0 and 6.5.

7 Claims, 1 Drawing Sheet

LOG REDUCTION OF ASPERGILLUS FUMIGATIS vs pH pH of Disinfecting Reaction
(Component A + Component B + 0.3 mol/L buffer + water)

LOG REDUCTION OF ASPERGILLUS FUMIGATIS vs pH

METHOD TO CLEAN AND DISINFECT PATHOGENS ON THE EPIDERMIS BY APPLYING A COMPOSITION CONTAINING PEROXIDASE, IODIDE COMPOUND AND SURFACTANT

This application is a continuation of prior U.S. application Ser. No. 515,332 filing date Apr. 27, 1990, now abandoned, which is a continuation of application Ser. No. 240,212 filing date Sept. 8, 1988, now abandoned.

FIELD OF THE INVENTION

This invention describes an epidermal cleaner for disinfecting pathogens on the surface of the skin which incorporates peroxidase, a source of peroxide and iodide to cause antiseptic disinfection in the presence of water.

The term "pathogen" is intended, for purposes of the present application, to specifically include bacteria and fungi, as well as other organisms, if present, particularly viruses and mycobacterium tuberculosis.

The epidermal cleaner is a viscous emollient formulation with a high concentration of surface active agents.

BACKGROUND OF THE INVENTION

Liquid skin cleaners contain a variety of surface active agents which perform several functions. These compositions generally contain surfactants, lathering agent(s), thickening agents, humectants and foam stabilizers. A disinfecting skin cleaner also contains antiseptic agents in combination with many or all of the preceding agents. The most commonly used antiseptic agents in disinfecting soaps are povidine-iodine (Disadine), chlorhexidine (Hibiscrub) and hexachlorophene (Phisohex).

The principle differences between conventional disinfecting soap compositions and the disinfecting epidermal cleaner of the present invention are (1) none of the components of this invention acting alone contribute a practical antiseptic activity to the product of this patent, (2) the inceptive bactericidal agent generated during the chemistry of this application is the free radical of iodide (or by-products) which is a fundamentally different chemistry from that of the antiseptic agents previously used in skin cleaners, and (3) the antiseptic activity of the disinfecting epidermal cleaner of the present invention does not cause irritation to the epidermis nor is it organoleptically aversive. The formulation of an emollient non-irritating antiseptic epidermal cleaner is only possible if the active antiseptic agents do not cause discomfort and are able to be formulated in an organoleptically unobjectionable medium.

The disinfecting epidermal cleaner as described in this specification is formulated to work upon admixture in an aqueous medium. Preferably a defined volume of water is admixed with the disinfecting components such that the individual components are diluted by 50 to 1000% upon use. That is, the concentration of the disinfecting epidermal cleaner of this application is designed to be diluted in water prior to use.

The essential constituents in commercial skin cleaning compositions are an antiseptic agent and a surfactant; however the final composition should exhibit high foaming, good water solubility, adequate detergency and acceptable organoleptic characteristics. Formulation of skin cleaning compositions containing conventional antiseptic agents has been problematical due to incompatibilities resulting from (1) destruction of the activity of said antiseptic agents, (2) phase incompatibility of said antiseptic agents, (3) long-term stability of said antiseptic agents in highly detergent compositions, and (4) achieving acceptable organoleptic properties. This application discloses the use of a composition containing peroxidase, peroxide and iodide in a prescribed formulation suitable for use as an antiseptic agent to form a disinfecting epidermal cleaner which does not suffer from the above incompatibilities.

For the peroxidase based composition of the subject invention to provide antiseptic activity in an epidermal cleaner the following must be-achieved: (1) the maintenance of enzymatic activity, (2) the maintenance of substrate (peroxide and iodide) concentrations within a defined range, (3) the absence of molecules or reaction by-products which meaningfully compete with iodide or peroxide for the active site of the enzyme, (4) the diffusion of the nascent bactericidal iodide radical (or by-product) from the enzyme's active site to targeted organisms, and (5) the absence of vitiating interactions between the bactericidal iodide free radicals and other components in the environment. The possibility of creating an effectual disinfecting epidermal cleaner whose biocidal ingredients are comprised of peroxidase, peroxide and iodide, can only be accomplished if the five requirements listed above are met.

It is known from Kessler (U.S. Pat. Nos. 4,476,108, 4,588,586 and 4,473,550), Orndorff (U.S. Pat. No. 4,370,199) and Montgomery (U.S. Pat. No. 4,576,817) that a biocidal formulation comprised of peroxidase, peroxide and a source of iodide is useful for disinfection in an aqueous non-viscous solution. The source of iodide must be ccapable of forming iodide ions upon dissolution in water in order for the system to function as a disinfectant. For purposes of the present invention non-viscous means a viscosity of less than 2.5 centipoises. The disinfecting applications described in the above identified patents take place either in a totally aqueous environment or upon a meaningful dilution or dissolution (greater than 10 fold) of a formulation to form a substantially aqueous environment. None of the previous applications involve disinfecting environments which are viscous and/or contain high concentrations of surface active agents required for a useful disinfecting epidermal cleaner.

The present invention may be used to disinfect any epidermal surface on either a human or animal. In fact, the present invention is particularly suited to the treatment of bovine mastitis.

The viscosity of commercial liquid soap cleaners are often at least about 5 centipoises and are typically above 20 centipoises and sometimes greater than 100 centipoises. The viscosity inherent to liquid skin cleaning compositions will reduce the diffusion of molecules relative to that in a substantially aqueous environment. The short-lived lifetime of the free radical generated by the removal of an electron from iodide imposes a constraint upon any system which uses peroxidase, peroxide and iodide as its active antiseptic agent. The free radicals generated at the active site of peroxidase must have enough time to diffuse to their ultimate site of action in order for the system to be effective. The diffusion coefficient, which is proportional to the rate of motion of a molecule in a matrix, is inversely proportional to the viscosity of a matrix. Every 10 fold increase in viscosity reduces the distance traveled of the iodide free radical per unit time by a factor of ten. Accordingly, the viscosity inherent in the high concentrations of surface active agents, including unsaturated fatty-acids, would be expected to decrease or eliminate the disinfecting ability of this system.

One skilled in the art of mechanistic organic chemistry would anticipate that the organic surface active agents of this invention would form a hostile environment for free radicals. A known parallel exists in the reduction or elimination of phenol catalyzed peroxidase/luminol chemiluminescence which is effected by the inclusion of molecules which interact with free radicals. In fact, any peroxidase catalyzed chemical event which requires the free radicals released into the environment from peroxidase to react with other molecules in solution can be affected by including exogenous organic material in the environment.

SUMMARY OF THE INVENTION

It has been discovered in accordance with the present invention that a composition of peroxidase, peroxide and a source of an iodide can form an antiseptic agent for use in a skin cleaner in the presence of water by controlling the pH of the aqueous composition between a pH of 3.0 to 6.5. The skin cleaner may have a high concentration of surface active agents and a viscosity above 2.5 centipoises. The epidermal cleaner of the present invention broadly comprises a surface active agent, an antiseptic agent including peroxidase, a source of peroxide, and an iodide compound in combination with a buffering system to cause a pH of between 3.0 and 6.5 when the cleaner is diluted with water over a dilution range of about 10 to 1 water to cleaner. The subject invention contemplates the use of any buffering system in conjunction with or without an inert carrier to cause equilibration of the composition in water with a pH in the final admixture of between 3.0 and 6.5 over a wide dilution range.

DETAILED DESCRIPTION OF THE INVENTION

Figure 1:
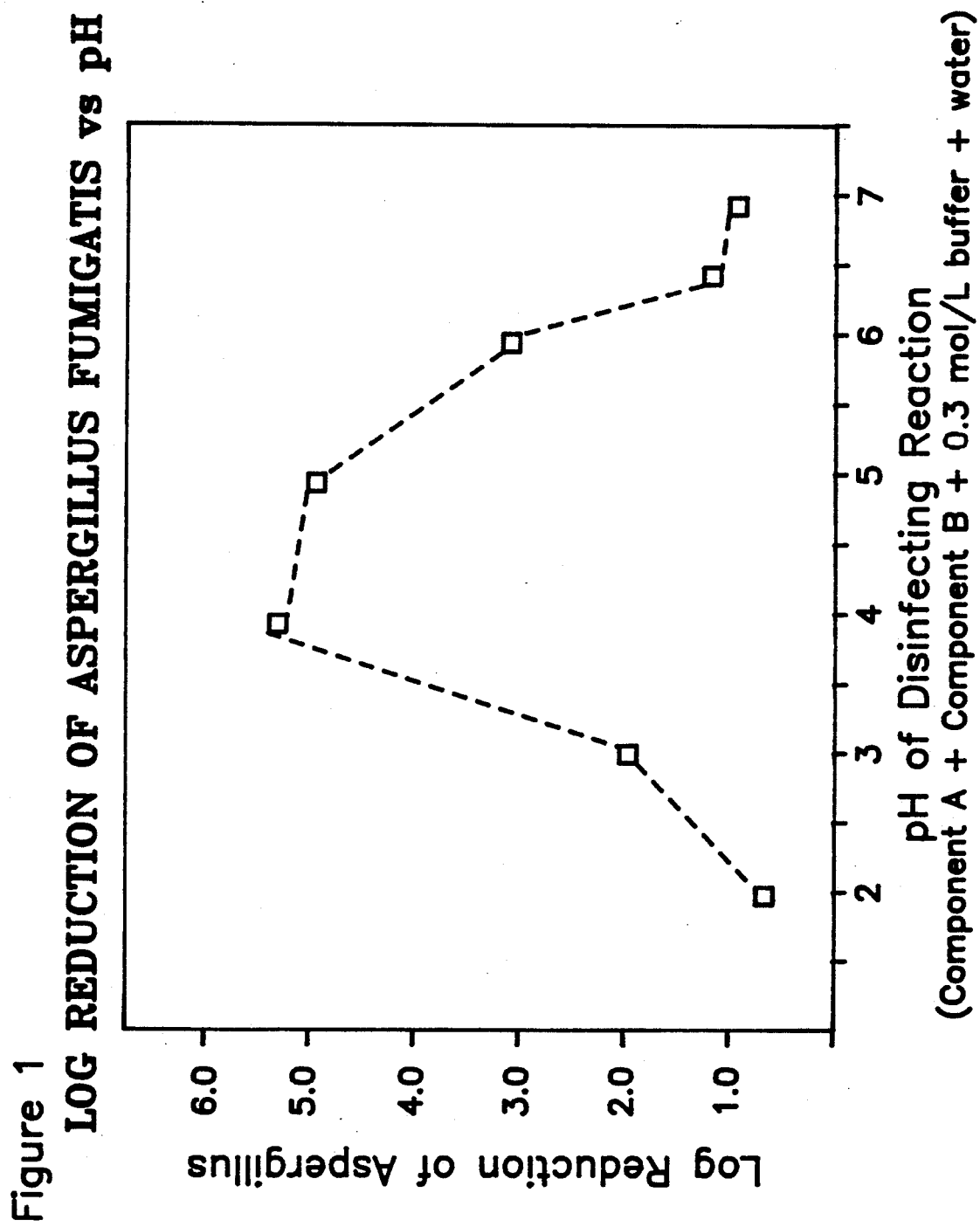
FIG. 1 shows the reduction in viable *Aspergillus fumigatis* in a liquid soap formulation as a function of pH over a five minute time period.

The disinfecting epidermal cleaner of the present invention comprises a surface active agent, an antiseptic agent formed from the combination of peroxidase, a source of iodide, a source of peroxide, and a buffering system to establish a controlled pH of between 3.0 to 6.5 when the skin cleaner is admixed with water. Peroxidase and iodide are stored in a buffered environment at a pH between 7.0 and 9.0. The buffering agents of the peroxidase component are at a concentration such that upon admixture with water and the buffered peroxide component, the pH of the final admixture is between 3.0 and 6.5. In practice this usually means that the concentration of the buffering agents in the peroxidase component is significantly lower than the concentration of pH controlling agents in the peroxide component; that is, the peroxidase containing component is weakly buffered. Peroxide is stored in a strongly buffered environment at a pH between 3.0 and 6.5. This patent discloses the ability of a peroxidase based disinfecting epidermal cleaner to work with a variety of known emollient and detergent agents.

Controlling the pH of the final reaction mixture is a critically important aspect of this invention. As can be seen in FIG. 1, the disinfecting activity of the epidermal skin cleaner is related to the pH in which the disinfecting reaction occurs. By controlling the pH of the reaction once all of the components have been admixed with water, the utility of the admixture is meaningfully enhanced. The disinfecting reaction takes place significantly more rapidly as the pH decreases from a pH of 7.0 to a pH 4.0. The preferred pH range is between 6.0 and 3.0 with an optimum pH range of 4.0 to 5.5. Below a pH of 3.0 the reaction appears to be less effective. This may be due to the stability of the enzyme at lower pH values. Although FIG. 1 deals only with *Aspergillus fumigatis*, the relative rate of inactivation at different pH values for other organisms will follow this trend since the shape of this curve is a function of the chemistry and independent of the organism. *Aspergillus fumigatis* was chosen because it is a difficult organism to inactivate.

The disinfecting epidermal cleaner of the instant invention is preferably formulated in two separate formulations which are combined with water immediately prior to use. The first formulation contains the enzyme peroxidase (Enzyme Commission Identification No. E.C. 1.11.1.7.) and an iodide compound in a weakly buffered composition, such as glycerol, at a pH between 7.0 and 9.0. The second formulation contains hydrogen peroxide in a strongly buffered composition. The two formulation are comprised such that when they are combined with water in the intended fashion, the pH of the final admixture is between 3.0 and 6.5. A source of iodide is contained only in the peroxidase containing component of the invention. Formulating peroxidase in combination with the iodide compound at a pH between 7.0 and 9.0 in glycerol or other suitable carriers like sucrose, maltose, maximizes the stability of the enzyme and iodide. Insuring a pH between 3.0 and 6.5 in the final antiseptic admixture, maximizes the speed, increases the shelf-life, and minimizes the cost of the final product. The surface active agents of the disinfecting epidermal cleaner of this invention consist of a class of molecules comprised of anionic, cationic, zwitterionic, non-ionic and ampholytic surface active agents. These molecules comprise a principal ingredient of presently used liquid soap and handcream formulations. Said molecules include sodium lauryl sulfate, lithium lauryl sulfate, alkyl benzenesulfonates, alkane sulfonates, alkene sulfonates, Tween 20-polyoxyethylene sorbitan monolaurate, Tween 100, alkyl sulphates, alkyl ether sulphates, polyoxyethylene condensation products or primary and secondary alcohols, fatty acid amides, block polymers of ethylene oxide and propylene oxide, myristic acid, lauric acid, capric acid, caprylic acid, coconut and palm kernel fatty acids, polyethoxylated glucosides and esters, hydroxy ethyl cellulose, hydroxy propyl quar, N-acyl-sarcosinates, sodium-N-acyl-N-methyl taurates, sodium cocoylisothioate, hydroxypropyl guar gum, amidopropyl betaines, and polyethylene glycol derivitives.

The donor molecule of this invention is iodide. Suitable sources of iodide for this invention include sodium iodide and potassium iodide as well as other salts of iodide. Any source of iodide or iodide compound which yields iodide ions upon dissolution in water, without yielding other deleterious effects to the activity of the system, is suitable for this application. The simple salts of iodide are preferred and have the advantage of being inexpensive. Additionally, they have a long shelf life both in solid and liquid form.

The peroxidase enzyme of this invention is identified by the International Union of Biochemistry and the International Union of Pure and Applied Chemistry by the Enzyme Commission identification No. E.C. 1.11.1.7. Peroxidase can be obtained from a wide variety of sources. The least expensive and most robust peroxidase suitable for this application is horseradish peroxidase. Commercially obtained peroxidase comes lyophilized as a dry powder which must then be admixed in a suitable carrier.

The preferred oxidant of this invention is hydrogen peroxide. Any material which acts as a source of peroxide when admixed in water is suitable for the present invention. This "source of peroxide" for purposes of the present invention means any material which can serve as precursors for hydrogen peroxide include metal peroxides, percarbonates, persulphates, perphosphates, peroxyesters, urea peroxide, peroxyacids, alkylperoxides, acylperoxides and perborates. Alternatively methyl peroxide can be formulated in the product. Mixtures of two or more of these substances can also be used.

The peroxidase containing component of the disinfecting epidermal cleaner of this application preferably includes a carrier such as glycerol although other carriers and combinations of carriers are possible. To maximize the shelf-life of the product it is necessary to include iodide compound in the peroxidase component of this invention and not to admix iodide in the peroxide containing component. Immediately prior to use, a defined volume of the peroxidase/iodide containing component and the peroxide/surfactant containing component are combined with water to form the active disinfecting epidermal cleaner of the instant invention. The formulations will function over a range of ratios of exogenously added water to peroxidase/iodide-peroxide/surfactant containing components. This ratio is based on volume to volume comparisons. The volume of water added divided by the sum of the volumes of the peroxidase/iodide-peroxide/surfactant containing components is between 0 5 and 10.

The peroxidase containing component of this invention consists essentially of water, carrier, the enzyme peroxidase, and a suitable buffering agent. The iodide salt is preferably added to the peroxidase component. The buffering agent tris-(hydroxymethyl)aminomethane at a final concentration between 1 and 10 mM at a pH between 7.0 and 9 0 and a calcium ion concentration between 2 and 25 mM is preferable. Sodium phosphate cannot be used either as the buffering agent or as an additive of the peroxidase containing component since it binds calcium and will, as a result, dramatically reduce the shelf-life of the product. Any compound or mixture of compounds which binds or sequesters calcium cannot be added to the peroxidase containing component.

The preferred carriers for the peroxidase containing component are sucrose, ethylene glycol, glycerol and other polyhydroxylated alkanes in which peroxidase has good stability. Carriers are present at a concentration of 5 to 45% w/v depending upon the selection of carrier(s) since different carriers have distinct properties. The preferred iodide salts for the peroxidase containing component is sodium iodide and potassium iodide. The concentration of iodide in the peroxidase containing component is between 0.00010 and 1300 mg/ml when the peroxidase containing component is diluted 1 to 4 immediately prior to use and preferably between 8 0 and 150 mg/ml when the peroxidase component is diluted 1 to 4 immediately prior to use.

The second component of the disinfecting epidermal cleaner of this patent contains peroxide in a broad concentration between 0.0003 and 3.0% weight to volume in a detergent based carrier component and in a preferred range of 0.1 and 0.003% when the peroxide containing component is diluted 1 to 4 immediately prior to use. Iodide may not be combined in this component as this will reduce the shelf life of the final product as iodide is known to be unstable at an acidic pH. The preferred detergent agents are sodium lauryl sulfate and lithium lauryl sulfate although many other detergents can be used and can be combined for admixture into the peroxide component of the disinfecting epidermal cleaner of this application. The concentration of the detergent depends upon which compound or mixtures of compounds are used and what the intended use is. Typically the concentration of detergents is between 5 and 25% of the peroxide formulation, although some formulations may have very low concentrations of detergent. The pH of the peroxide containing component is carefully controlled so that it is between pH 3.0 and 6.5. The concentration of buffer used in the peroxide containing component is preferably between 0.100 and 1.0 molar in the peroxide containing component. Sodium phosphate is the buffer of choice for the peroxide containing component since its cost is low; however, the concentration of buffering component will vary depending upon which buffer is used.

The critical aspect of the buffering of the peroxide containing component is that the buffer must be concentrated enough to control the pH of the final admixture within a pH range between a pH 3.0 and 6.5 when admixed with defined portions of the peroxidase/iodide component and peroxide component and portions of water which vary from 50 percent to ten times the combined volumes of the peroxidase/iodide and peroxide components.

The peroxide containing component of the disinfecting epidermal cleaner of this application can contain a variety of nonessential optional ingredients suitable for rendering such compositions more desirable. Such common ingredients are familiar to those skilled in the art and include preservatives, viscosity modifiers, coloring agents, pH controlling agents, suspending agents, sequestering agents, perfumes and opacifiers. However, no sequestering agents or any agent which bind calcium can be included in the peroxidase containing component. Agents commonly used as preservatives which are compatible with the chemistry of this application include include benzyl alcohol, methyl paraben, sorbic acid. Carboxymethyl cellulose, ethylcellulose, polyvinyl alcohol and guar gum derivatives are commonly used as thickeners and can be used with the formulations of this application. Phosphoric acid, sodium phosphate, sodium hydroxide, tris-(hydroxymethyl)aminomethane as pH controlling agents. Magnesium/aluminum silicate as suspending agents and ethylenediaminetetraacetic acid as a sequestering agent.

EXAMPLES

Example 1

Component A, the peroxidase containing component, consisted of 0.4 mg/ml of Sigma Type I peroxidase, 4 mg/ml acetylated BSA, 2 mg/ml sodium iodide, 0.2 mg/ml calcium chloride, 1 mM tris-(hydroxymethyl- )aminomethane (pH 7.2), and 20% glycerol. Component B, the peroxide containing component, consisted of 0.0038% hydrogen peroxide, 2.5% sodium lauryl sulfate, 0.125 mg/ml ethylenediaminetetraacetic and 0.125 mg/ml of sorbic acid. Four ml of component B was added to 1 ml of several phosphate buffers each of which was 0.4 molar. The pH of the 0.4 molar phosphate buffers was 4.0, 4.5, 5.5 and 6.5.

Cultures of *Listeria selegeri, E. coli,* and *Salmonella typhimurium* were spun down in a clinical centrifuge and washed in normal saline. Equal volumes of component A (1 ml) and component B (1 ml) were added to 1 ml of these bacterial suspensions and mixed. Aliquots were withdrawn every 20 seconds and diluted in 10 mg/ml sodium fluoride. Serial dilutions of each time point were made and the CFU per ml was determined. The rate of inactivation in viable organisms per unit time was calculated by taking the logarithm of the ratio of the number of viable organisms at the start of the reaction divided by the number of organisms which were viable at the end of the reaction and dividing this ratio by the time of the reaction.

| *Listeria selegeri* | | | | |
|---|---|---|---|---|
| 4.0 | 4.5 | 5.5 | 6.5 | pH |
| 0.16 | 0.092 | 0.076 | 0.059 | Rate of Inactivation |
| *E. coli* | | | | |
| 4.0 | 4.5 | 5.5 | 6.5 | pH |
| 0.12 | 0.11 | 0.087 | 0.077 | Rate of Inactivation |
| *Salmonella typhimurium* | | | | |
| 4.0 | 4.5 | 5.5 | 6.5 | pH |
| 0.15 | 0.10 | 0.093 | 0.077 | Rate of Inactivation |

Each of the organisms were inactivated. The lower pH values yielded a more rapid inactivation. When the concentration of sodium lauryl sulfate was increased 10 fold, all of the organisms were inactivated within 40 seconds.

Example 2

Component A, the peroxidase containing component, consisted of 1.0 mg/ml of Sigma Type I peroxidase, 30% sucrose, 6 mg/ml sodium iodide, 1.0 mg/ml calcium chloride, 5 mM tris-(hydroxymethyl)aminomethane (pH 7.5), and 4 mg/ml sodium chloride. Component B, the peroxide containing component, consisted of 0.0030% hydrogen peroxide, 1.0% cetyl alcohol, and 1.0% Brij-35 Four ml of component B was added to 1 ml of several phosphate buffers each of which was 0.3 molar. The pH of the 0.3M phosphate buffers was 4.0, 4.5, 5.5 and 6.5.

Cultures of *Staphlococcus aureus, Staphlococcus epidermitis,* and *Salmonella typhimurium* and *Listeria selegeri* were spun down in a clinical centrifuge and washed in normal saline Equal volumes of component A (1 ml) and component B (1 ml) were added to 1 ml of these bacterial suspensions and mixed. Aliquots were withdrawn every 20 seconds and diluted in 10 mg/ml sodium fluoride. Serial dilutions of each time point were made and the CFU per ml was determined. The rate of inactivation of viable organisms per unit time was calculated by taking the logarithm of the ratio of the number of viable organisms at the start of the reaction divided by the number of organisms which were viable at the end of the reaction and dividing this ratio by the time of the reaction. Each of the organisms was inactivated. The lower pH values yielded a more rapid inactivation. When the concentration of Brij-35 and cetyl alcohol was increased tenfold, the rate of inactivation at a pH of 6.0 was increased.

| *Listeria monocytogenes* | | | | |
|---|---|---|---|---|
| 3.5 | 4.5 | 5.5 | 6.5 | pH |
| 0.22 | 0.077 | 0.055 | 0.003 | Rate of Inactivation |
| *S. aureus* | | | | |
| 3.5 | 4.5 | 5.5 | 6.5 | pH |
| 0.006 | 0.003 | 0.002 | 0.002 | Rate of Inactivation |
| *Salmonella typhimurium* | | | | |
| 3.5 | 4.5 | 5.5 | 6.5 | pH |
| 0.13 | 0.06 | 0.045 | 0.034 | Rate of Inactivation |
| *S. epidermidis* | | | | |
| 3.5 | 4.5 | 5.5 | 6.5 | pH |
| 0.125 | 0.088 | 0.043 | 0.030 | Rate of Inactivation |

Example 3

The effect of pH between 2 0 and 7.0 on the inactivation of *Aspergillus fumigatis* with a disinfecting epidermal skin cleaner was examined. The peroxidase component (component A) contained 1.0 mg/ml of sodium iodide, 20.0 percent glycerol, 5.0 mg/ml of sodium chloride, 1.1 mg/ml of calcium chloride, 0.5 mg/ml of peroxidase (Sigma Type I) in 10 mM tris-(hydroxymethyl)aminomethane. The peroxide component (component B) contained 0.03 percent hydrogen peroxide, 1.0 mg/ml of ethylenediaminetetraacetic, and 1.8 percent of sodium-lauryl-sulfate in water. Immediately prior to use, component B was mixed with 0.20 mol/L buffers which had been equilibrated at the desired pH values. For a pH value in the disinfecting admixture of 7.0, 6.5, and 6.0, sodium phosphate was used as the buffer for mixture with component B. For a pH value in the disinfecting admixture of 5.0, and 4.0, citric acid - sodium phthalate was used as the buffer for mixture with component B. For a pH value in the disinfecting admixture of 3.0 and 2.0, phthalic acid - sodium phthalate was used as the buffer for mixture with component B.

*Aspergillus fumigatis* in 0.125 ml (4,000,000 CFU) was added to 0.50 ml of component A. A one part to one part mixture of component B with each buffer was added (0.50 ml) to 2.0 ml of water and mixed. These two mixtures were added and incubated at room temperature for 5 minutes. Samples were removed (0.10 ml) and diluted into 0.30 mol/L sodium phosphate, pH 7.0 which was 0.30 mol/L with respect to sodium fluoride. This suspension and serial dilutions of this mixture (0.10 ml) were spread on Sabouraud dextrose/agar plates and incubated for three days at 42 degrees centigrade. The log reduction over the five minute time period was calculated (FIG. 1) by subtracting the logarithm of the number of viable organisms at the end of the reaction from the logarithim of the number of organisms at the start of the reaction which were viable at the end of the reaction.

| *Aspergillus fumigatis* Log Reduction per 10 Minutes | | | | | | | |
|---|---|---|---|---|---|---|---|
| pH | 2.0 | 3.0 | 4.0 | 5.0 | 6.0 | 6.5 | 7.0 |
| log Reduction | 1.3 | 2.0 | 5.4 | 5.0 | 3.2 | 1.2 | 1.0 |

*Aspergillus fumigatis* was inactivated at each pH value. The lower pH values yielded a greater degree of inactivation. The inactivation at pH 2.0 was not as rapid as the inactivation at 3.0 or 4.0. It is likely that the enzyme is inactivated at this pH value. When the concentration of sodium-lauryl-sulfate was increased 10 fold there was a 6 log reduction at a pH of 5.0.

What is claimed is:

1. A method for topically treating skin to simultaneously clean and disinfect pathogens on the epidermis comprising the steps of:
   (a) combining a peroxidase with an iodide compound which will provide a source of iodide ions in water to form a first component;
   (b) combining a source of peroxide with a surface active agent(s) selected from the class consisting of anionic, cationic, zwitterionic, non-ionic and ampholytic molecules to form a second component;
   (c) adding buffer means to either said first or second components, or to both said first and second components, to control the pH of an aqueous admixture of said first and second components in a range of between a pH of 3.0 and about 6.5;
   (d) admixing said buffered first and second components with a defined volume of water such that a buffered aqueous admixture is formed within said pH range, with said buffered first and second components diluted between about fifty percent (50%) to one thousand percent (1000%); and
   (e) contacting the surface of the skin to be treated with said aqueous admixture.

2. A method, as defined in claim 1, wherein said first component is an aqueous solution comprising a peroxidase selected from the Enzyme Commission identification No. E.C., 1.11.1.7, a buffering agent, a carrier and said iodide compound.

3. A method, as defined in claim 2, wherein said iodide compound is a salt of iodide in a concentration of 0.00010 and 1300 mg/ml of said first component.

4. A method, a defined in claim 3, wherein the pH of said first component is adjusted to between a pH of 7.0 and 9.0.

5. A method, as defined in claim 4, wherein said carrier is selected from the class consisting of sucrose, ethylene glycol, glycerol and other polyhydroxylated alkanes.

6. A method, as defined in claim 4, wherein said peroxide in said second component lies in a concentration of between 0.0003 and 3.0 percent weight to volume relative to said surface active agent(s).

7. A method for simultaneously cleaning and disinfecting pathogens on the epidermis in the treatment of bovine mastitis comprising the steps of:
   forming an aqueous, antiseptic solution consisting essentially of: a source of hydrogen peroxide, an iodide compound which forms iodide ions in water, a peroxidase selected from the Enzyme Commission Classification No. 1.11.17, buffer means, surface active agents, and water, with the concentration of said buffer means sufficient to maintain the pH of the solution between a pH of 3 and 6.5, and with the concentration of water representing from 50 percent to ten times the combined volume of the peroxidase, iodide, and peroxide components; and
   contacting the epidermal area to be treated with said aqueous solution.

* * * * *